US010101257B2

(12) United States Patent
Yazawa et al.

(10) Patent No.: US 10,101,257 B2
(45) Date of Patent: Oct. 16, 2018

(54) PARTICULATE DETECTION APPARATUS AND PARTICULATE DETECTION SYSTEM

(71) Applicant: NGK SPARK PLUG CO., LTD., Nagoya-shi, Aichi (JP)

(72) Inventors: Katsunori Yazawa, Kasugai (JP); Kaoru Hisada, Obu (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 142 days.

(21) Appl. No.: 15/198,633

(22) Filed: Jun. 30, 2016

(65) Prior Publication Data

US 2017/0010201 A1 Jan. 12, 2017

(30) Foreign Application Priority Data

Jul. 6, 2015 (JP) ................................. 2015-135444
Mar. 24, 2016 (JP) ................................. 2016-060269

(51) Int. Cl.
*G01N 33/00* (2006.01)
*G01N 15/06* (2006.01)
*F01N 13/00* (2010.01)
*F01N 11/00* (2006.01)
*G01N 15/00* (2006.01)

(52) U.S. Cl.
CPC ....... *G01N 15/0656* (2013.01); *F01N 13/008* (2013.01); *G01N 33/0073* (2013.01); *F01N 11/00* (2013.01); *F01N 2560/05* (2013.01); *F01N 2900/1402* (2013.01); *F01N 2900/1406* (2013.01); *F01N 2900/1411* (2013.01); *G01N 2015/0046* (2013.01)

(58) Field of Classification Search
CPC ............ G01N 15/0656; G01N 33/0073; G01N 33/0006; G01N 2015/0046; F01N 13/008; F01N 11/00; F01N 2900/1402; F01N 2560/05; F01N 2900/1406; F01N 2900/1411
USPC .. 73/1.06, 1.07, 23.32, 23, 33, 28.01–28.06, 73/114.71, 114.72, 865.5; 356/438, 439
See application file for complete search history.

(56) References Cited

U.S. PATENT DOCUMENTS

| 4,212,190 A | * | 7/1980 | Coover ................ G01N 29/046 73/24.03 |
| 4,543,815 A | * | 10/1985 | Troup .................. G01N 21/534 340/628 |
| 8,505,276 B2 | * | 8/2013 | Nakamura .............. F01N 11/00 60/276 |
| 2007/0097372 A1 | * | 5/2007 | Itagaki .................. A47L 9/2815 356/437 |

(Continued)

FOREIGN PATENT DOCUMENTS

JP 2012-194079 A 10/2012

*Primary Examiner* — Robert R Raevis
(74) *Attorney, Agent, or Firm* — Sughrue Mion, PLLC

(57) ABSTRACT

A particulate detection apparatus (3) controls a particulate sensor (2) for detecting the amount of particulates contained in exhaust gas and which has a pump (203) for supplying air to a detection section of the particulate sensor (2) into which the exhaust gas is introduced. The particulate detection apparatus (3) detects the flow rate of air supplied from the pump (203) to the particulate sensor (2) by a flow rate sensor (207). The particulate detection apparatus (3) maintains a consistent detection accuracy of the particulate sensor (2) based on the result of the detection by the flow rate sensor (207).

10 Claims, 12 Drawing Sheets

(56) References Cited

U.S. PATENT DOCUMENTS

2008/0127633 A1* 6/2008 Kesse .................. F01N 11/00
   60/277
2011/0050243 A1   3/2011 Tikkanen
2014/0019077 A1* 1/2014 Berghof ................ G01D 3/022
   702/100

* cited by examiner

PARTICULATE DETECTION APPARATUS AND PARTICULATE DETECTION SYSTEM

BACKGROUND OF THE INVENTION

1. Field of the Invention

The present invention relates to a particulate detection apparatus and to a particulate detection system for detecting the amount of particulates contained in a gas under measurement.

2. Description of the Related Art

Conventionally, a particulate detection system has been known which includes a particulate sensor for detecting the amount of particulates (for example, soot) contained in exhaust gas discharged from an internal combustion engine and which is configured to supply high-pressure air to the particulate sensor so as to drive the particulate sensor (see, for example, Patent Document 1).

[Patent Document 1] Japanese Patent Application Laid-Open (kokai) No. 2012-194079

3. Problem to be Solved by the Invention

In such a particulate detection system, the detection accuracy of the particulate sensor is possibly influenced by a change in the amount of air supplied to the particulate sensor, which change occurs due to fluctuation in the temperature or humidity of an environment under which a pump for supplying high-pressure air is used, fluctuation of power supply voltage supplied to the pump, or pressure fluctuation at a location where the sensor is installed (for example, inside an exhaust pipe of a vehicle).

SUMMARY OF THE INVENTION

The present invention has been made in order to address the above problem, and an object thereof is to provide a technique for improving the detection accuracy of a particulate sensor.

The above object of the present invention has been achieved by providing (1) a particulate detection apparatus which controls a particulate sensor for detecting the amount of particulates contained in a gas under measurement and which includes a gas supply section for supplying a gas to a detection section of the particulate sensor into which the gas under measurement is introduced. The particulate detection apparatus includes gas detection means and maintenance means.

The gas detection means detects at least one of the flow rate and pressure of the gas supplied from the gas supply section to the particulate sensor. The maintenance means maintains, based on the result of the detection by the gas detection means, a desired accuracy in detecting the amount of particulates by the particulate sensor.

The particulate detection apparatus (1) of the present invention configured as described above detects at least one of the flow rate and pressure of the gas, which correlates with the amount of the gas supplied to the particulate sensor, to thereby maintain a desired accuracy in detecting the amount of the particulates by the particulate sensor. Therefore, the particulate detection apparatus of the present invention can suppress a decrease in detection accuracy due to a change in the amount of the gas supplied to the particulate sensor, which change may occur due to (i) fluctuation of the temperature or humidity of an environment under which the particulate detection apparatus, including the gas supply section, is used, (ii) fluctuation of power supply voltage supplied to the gas supply section, or (iii) pressure fluctuation at a location where the sensor is installed (around the detection section), whereby the detection accuracy of the particulate sensor can be improved.

The detection accuracy in the particulate detection apparatus of the present invention is determined as follows. Under an environment in which the amount of particulates contained in the gas under measurement is maintained constant, the amount of particulates is detected by the particulate sensor a plurality of times. The detection accuracy is determined based on the ratio of the number of times that the particulate sensor outputs the same detection result to the plurality (number) of times that the particulate amounts were detected. Further, the detection accuracy can be quantified, for example, in terms of the standard deviation of the detection results.

In a preferred embodiment (2), the particulate detection apparatus (1) further comprises adjustment means for adjusting the at least one of the flow rate and pressure of the gas supplied from the gas supply section to the particulate sensor, and the maintenance means controls the adjustment means based on the result of the detection by the gas detection means so as to maintain the at least one of the flow rate and pressure of the gas at a target value set in advance.

In a preferred embodiment (3) of the particulate detection apparatus (1), the maintenance means maintains the detection accuracy by correcting the result of the detection by the particulate sensor based on the result of the detection by the gas detection means.

In another preferred embodiment (4) of the particulate detection apparatus (1), in order to maintain a consistent detection accuracy, the maintenance means controls the gas supply section based on the result of the detection by the gas detection means so as to maintain the at least one of the flow rate and pressure of the gas at a target value set in advance.

In yet another preferred embodiment (5), the particulate detection apparatus of any of (1) to (4) above comprises warning means for issuing a warning when a state, in which at least one of the flow rate and pressure of the gas falls outside an allowable range set in advance, continues for at least a warning judgment time set in advance. In this case, the particulate detection apparatus can alert a user of the particulate detection apparatus to the occurrence of an anomaly; i.e., the continuation of a state in which at least one of the flow rate and pressure of the gas falls outside the allowable range. Therefore, the particulate detection apparatus can restrain the continuation of a state in which the detection accuracy of the particulate sensor has decreased due to a change in the amount of the gas, to thereby improve the detection accuracy of the particulate sensor.

In yet another preferred embodiment (6), the particulate detection apparatus of any of (1) to (5) above further comprises a humidity adjustment section for adjusting humidity of the gas supplied from the gas supply section and flowing through a gas flow passage. In this case, the particulate detection apparatus can suppress a change in the detection accuracy of the particulate sensor due to a change in the humidity of the gas.

In yet another preferred embodiment (7) of the particulate detection apparatus (6), the humidity adjustment section is disposed in the gas flow passage, the gas flow passage being located between the gas supply section and the gas detection means. In this case, even when at least one of the flow rate and pressure of the gas changes as a result of passage of the gas through the humidity adjustment section, the particulate detection apparatus can detect that change by the gas detection means. Therefore, the particulate detection apparatus can suppress a decrease in detection accuracy due to the above-described change generated as a result of passage of the gas through the humidity adjustment section, to thereby improve the detection accuracy of the particulate sensor.

In yet another preferred embodiment (8), the particulate sensor of any of (1) to (7) above includes a gas jetting source which generates ions by means of corona discharge and jets the generated ions into the detection section together with the gas supplied from the gas supply section, and the particulate detection apparatus includes power supply means for supplying electric power for producing the corona discharge. In this case, even when the amount of the gas changes, the ions generated by means of corona discharge can be reliably jetted to the detection section of the particulate sensor. Thus, it is possible to avoid the continuation of a state in which the accuracy in detecting particulates through use of ions has decreased.

In yet another preferred embodiment (9), the particulate sensor of any of (1) to (8) above is a direct-insertion sensor which is inserted directly into an exhaust pipe through which exhaust gas discharged from an internal combustion engine flows, or into a gas flow pipe attached to an outlet side of the exhaust pipe, so as to detect the amount of particulates contained in the exhaust gas. Further, the particulate detection apparatus is connected to the particulate sensor via a gas flow passage through which the gas supplied from the gas supply section flows. In this case, the particulate detection apparatus of the present invention can detect the amount of particulates contained in the exhaust gas without introducing the exhaust gas into the interior of the particulate detection apparatus.

In a second aspect (10), the present invention provides a particulate detection system which comprises the particulate detection apparatus of any of (1) to (9) above and a particulate sensor connected thereto, the particulate apparatus controlling the particulate sensor for detecting an amount of particulates contained in a gas under measurement. Therefore, this aspect of the present invention can provide a particulate detection system which avoids a reduction in detection accuracy of the amount of particulates.

DESCRIPTION OF REFERENCE NUMERALS

Figure 1:
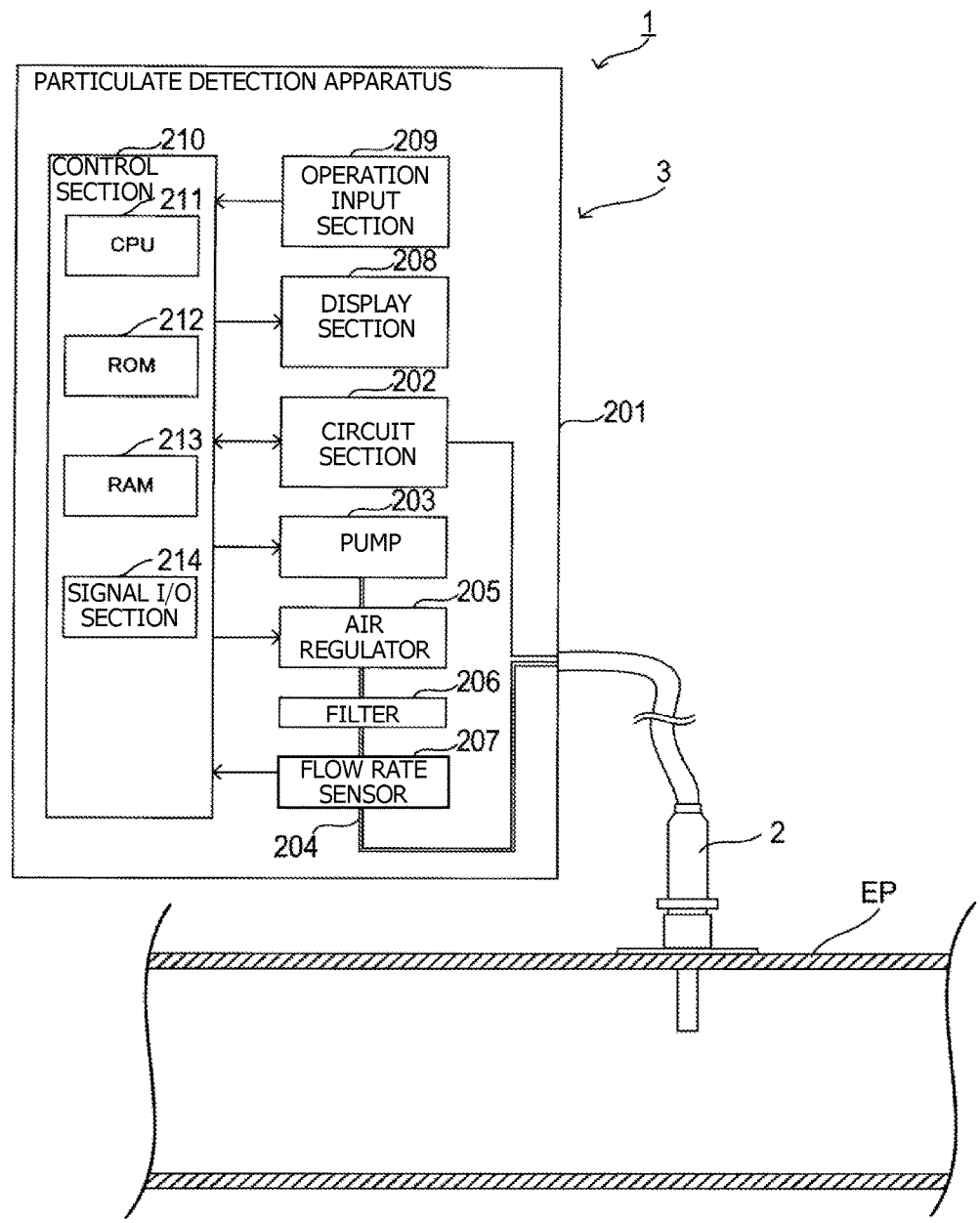
FIG. 1 is a diagram schematically showing the configuration of a particulate detection system 1 of a first embodiment.

Reference numerals used to identify various features in the drawings include the following.
1 . . . particulate detection system, 2 . . . particulate sensor, 3 . . . particulate detection apparatus, 10, 20 . . . electrode, 30 . . . ion trapping section, 40 . . . exhaust gas electrification section, 46 . . . nozzle, 50 . . . ion generation section, 202 . . . circuit section, 203 . . . pump, 204 . . . air flow passage, 205 . . . air regulator, 206 . . . filter, 207 . . . flow rate sensor, 208 . . . display section, 209 . . . operation input section, 210 . . . control section, 211 . . . CPU, 212 . . . ROM, 213 . . . RAM, 214 . . . signal input/output section, 216 . . . drier, 220 . . . primary side power supply section, 230 . . . secondary side power supply section, 231 . . . current supply circuit, 232 . . . current supply circuit, 240 . . . current difference measurement section

DETAILED DESCRIPTION OF THE PREFERRED EMBODIMENTS

The present invention will now be described in detail with reference to the drawings. However, the present invention should not be construed as being limited thereto.
(First Embodiment)

As shown in FIG. 1, a particulate detection system 1 of an embodiment to which the present invention is applied includes a particulate sensor 2 and a particulate detection apparatus 3.

The particulate sensor 2 is attached to an exhaust pipe EP of an internal combustion engine of a vehicle and detects the amount of particulates (e.g., soot) contained in exhaust gas within the exhaust pipe EP.

The particulate detection apparatus 3 includes a housing 201, a circuit section 202, a pump 203, an air flow passage 204, an air regulator 205, a filter 206, a flow rate sensor 207, a display section 208, an operation input section 209, and a control section 210.

The housing 201 has a box-like shape and accommodates the circuit section 202, the pump 203, the air flow passage 204, the air regulator 205, the filter 206, the flow rate sensor 207, the display section 208, the operation input section 209, and the control section 210. Notably, the housing 201 is configured such that a user can carry the housing 201. Therefore, the user can carry the housing 201 to the location of a vehicle to which the particulate sensor 2 is to be attached, and attach the particulate sensor 2 to the vehicle for use of the particulate detection system.

The circuit section 202 drives the particulate sensor 2 and detects the amount of particulates contained in the exhaust gas based on a detection signal from the particulate sensor 2.

The pump 203 produces high-pressure air used for driving the particulate sensor 2.

The air flow passage 204 supplies the high-pressure air produced by the pump 203 to the particulate sensor 2.

The air regulator 205 adjusts the flow rate of the high-pressure air supplied from the pump 203 through the air flow passage 204 in accordance with an air regulator control value indicated by an air regulator control signal input from the control section 210.

The filter 206 removes dust, etc., contained in the high-pressure air flowing through the air flow passage 204.

The flow rate sensor 207 detects the flow rate of the high-pressure air flowing through the air flow passage 204.

The display section 208 includes a display unit disposed on the housing 201 and displays various images on the display screen of the display unit.

The operation input section 209 includes switches disposed on the housing 201 and outputs input operation information for specifying an input operation which is performed by the user via the switches.

The control section 210 is mainly composed of a microcomputer including a CPU 211, a ROM 212, a RAM 213, a signal input/output section 214, etc. The control section 210 executes various types of processes based on inputs from the circuit section 202, the flow rate sensor 207, and the operation input section 209, and controls the circuit section 202, the pump 203, the air regulator 205, and the display section 208.

Figure 2:
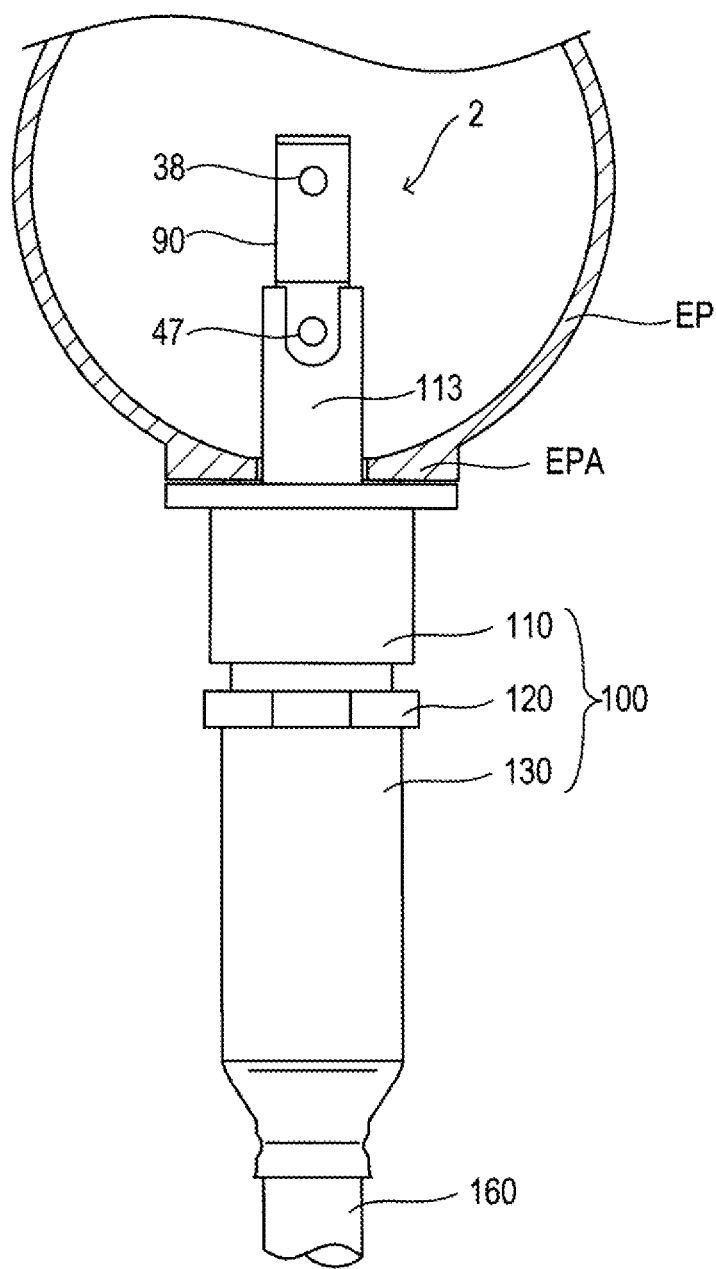
FIG. 2 is a plan view of a particulate sensor 2 attached to an exhaust pipe.

As shown in FIG. 2, the particulate sensor 2 includes an inside metallic member 90, an outside metallic member 100, and a cable 160.

The inside metallic member 90 is formed of metal to have a circular columnar outer shape and has a gas discharge opening 38 (described below) and a gas introduction opening 47 (described below). The inside metallic member 90 electrically communicates with a portion (location) of the circuit section 202 which is maintained at a first potential (a potential different from a ground potential) through the cable 160, whereby the inside metallic member 90 is maintained at the first potential.

The outside metallic member 100 supports the inside metallic member 90 in a state in which the gas discharge opening 38 and the gas introduction opening 47 are exposed. The outside metallic member 100 is fixed to an attachment portion EPA provided on the outer periphery of the exhaust pipe EP such that a portion of the inside metallic member 90 projects from the inner wall of the exhaust pipe EP. Notably, the outside metallic member 100 is attached to the exhaust pipe EP maintained at the ground potential (a second potential different from the first potential), whereby the outside metallic member 100 is maintained at the ground potential.

Figure 3:
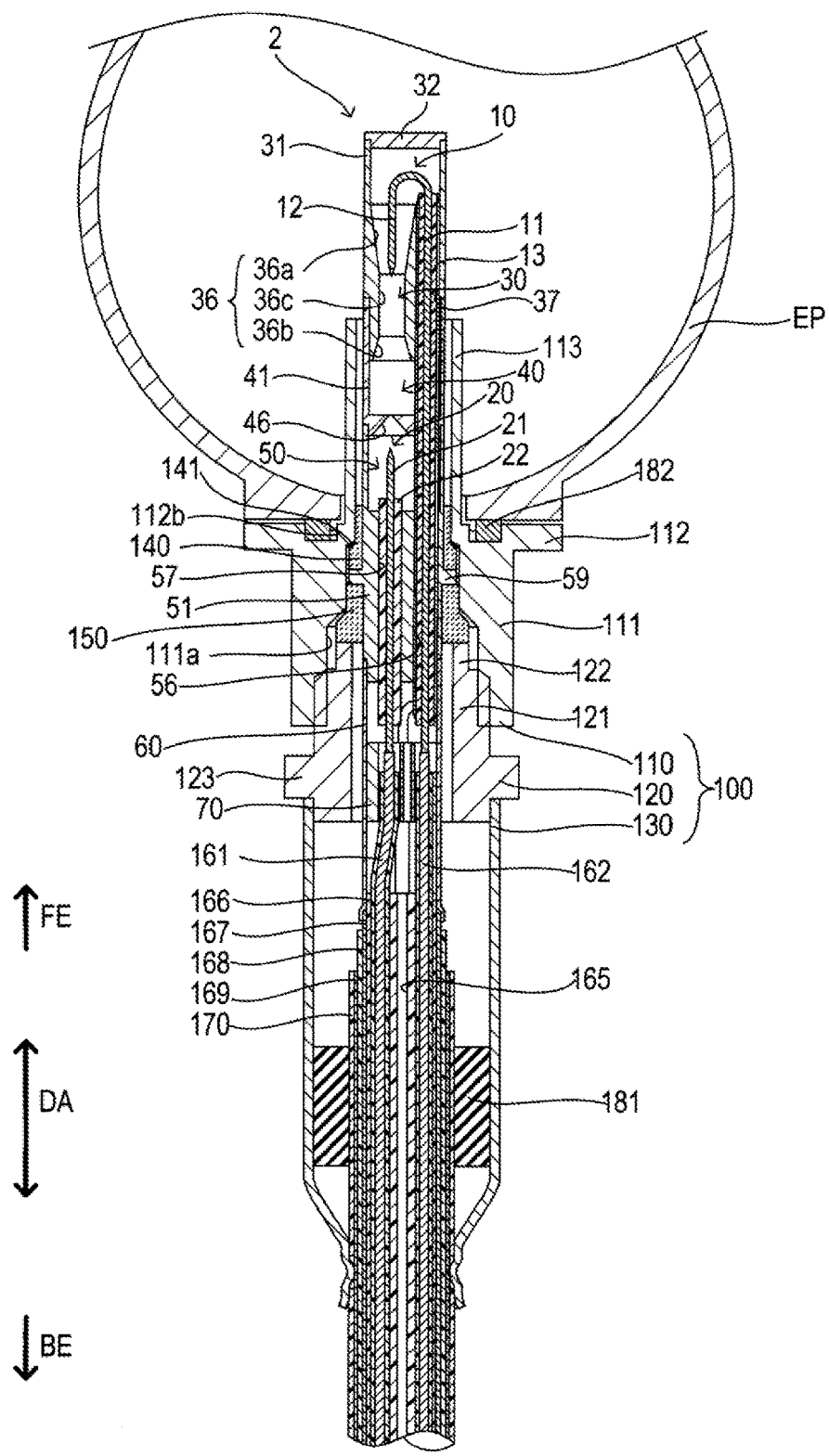
FIG. 3 is a sectional view of the particulate sensor 2.
Figure 4:
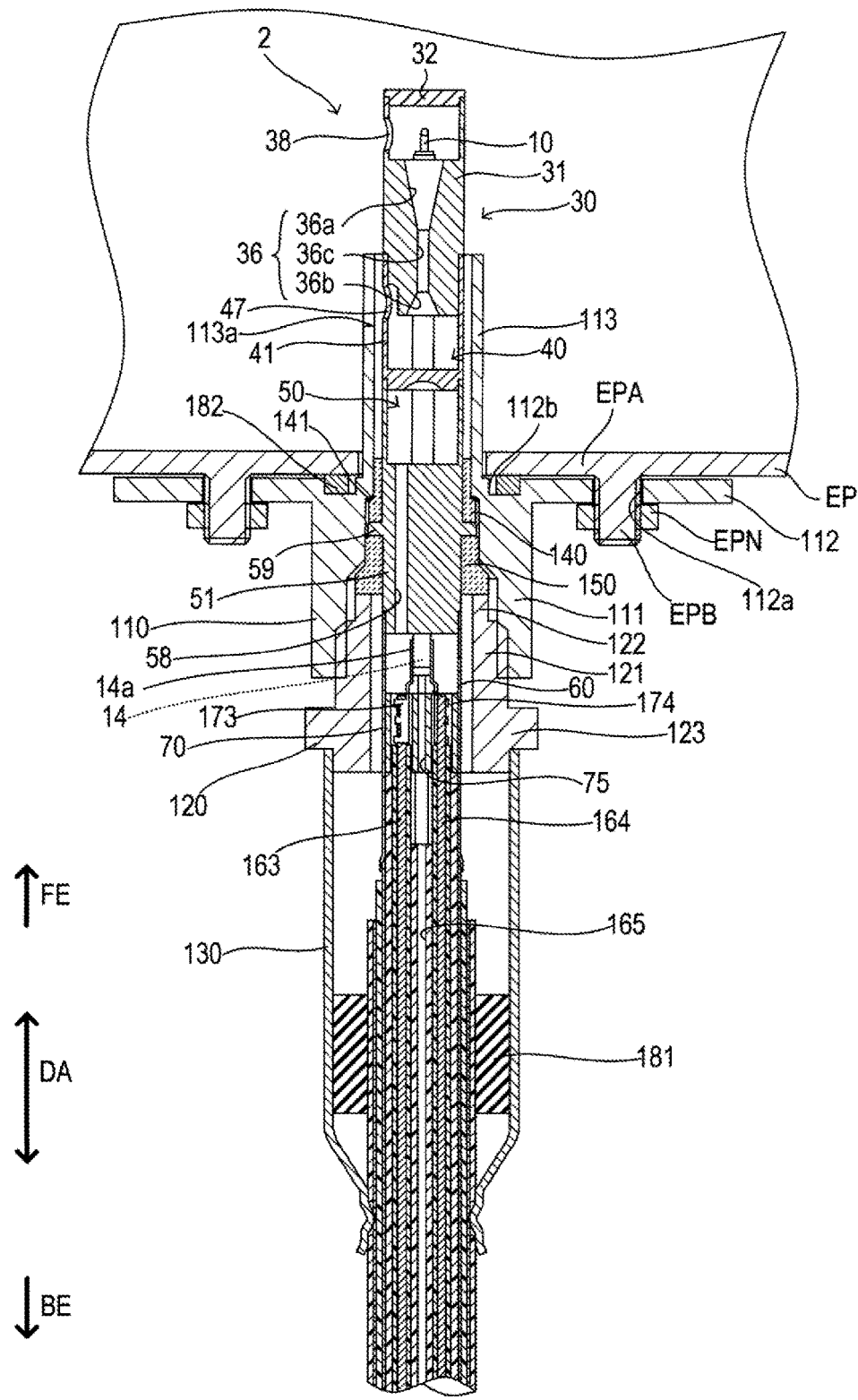
FIG. 4 is a sectional view of the particulate sensor 2.
Figure 5:
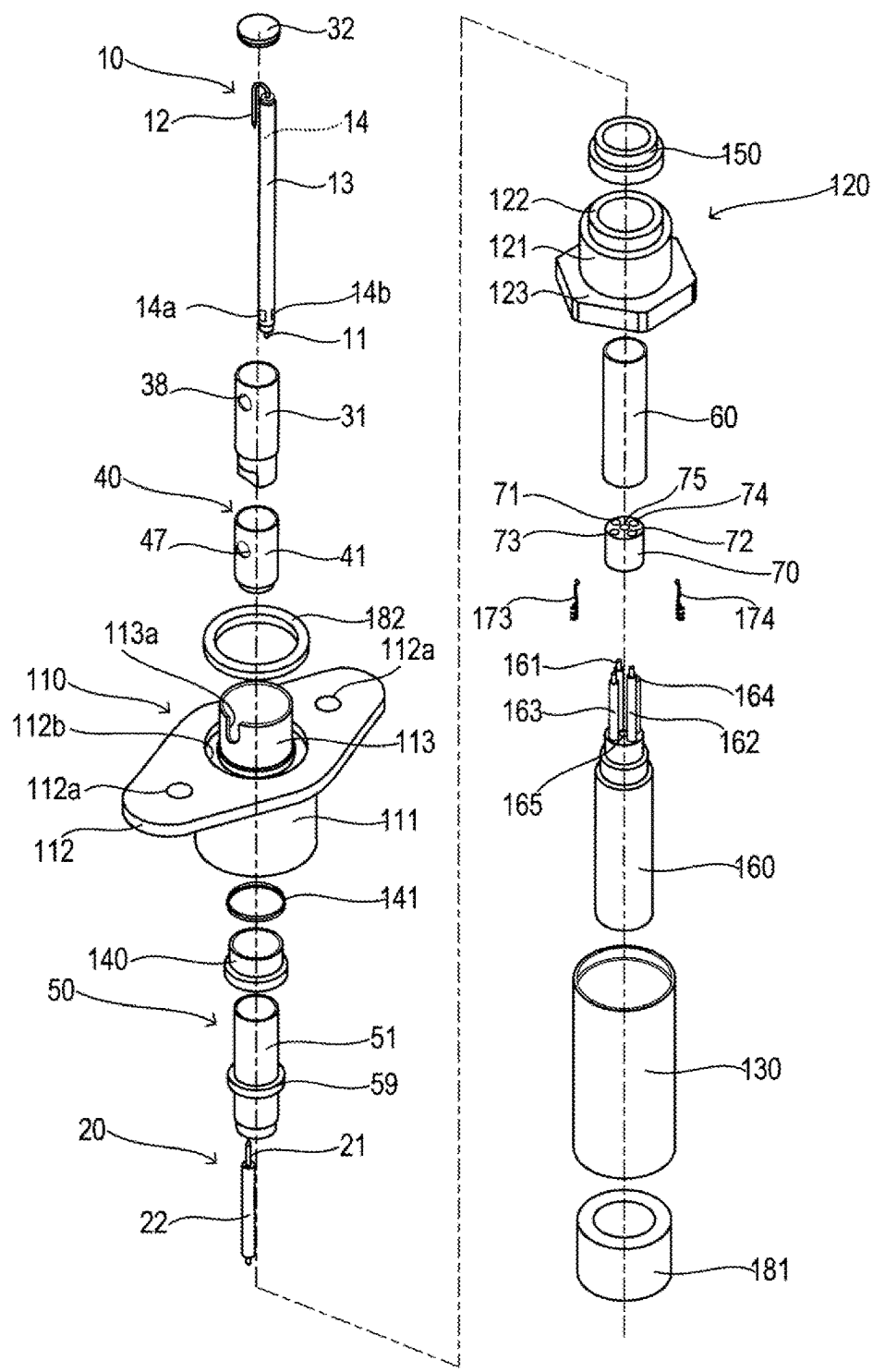
FIG. 5 is an exploded perspective view of the particulate sensor 2.

FIGS. 3 and 4 are sectional views of the particulate sensor 2 attached to the exhaust pipe EP. FIG. 3 shows a cross section perpendicular to a direction in which the exhaust pipe EP extends. FIG. 4 shows a cross section along the direction in which the exhaust pipe EP extends. FIG. 5 is an exploded perspective view of the particulate sensor 2. In FIGS. 3 to 5, the upper end side of the particulate sensor 2 will be referred to as the "forward end side FE," and the lower end side of the particulate sensor 2 will be referred to as the "back end side BE."

As shown in FIGS. 3 to 5, the particulate sensor 2 includes electrodes 10 and 20, an ion trapping section 30, an exhaust gas electrification section 40, and an ion generation section 50.

The electrode 10 includes a main body portion 11, a curved portion 12, an insulating pipe 13, and a heater 14. The main body portion 11 is a rod-shaped member formed of stainless steel and extends in an axial direction DA. The curved portion 12 is a member formed of stainless steel, extending from an end of the main body portion 11 on the forward end side FE, and bent into a U-like shape. The insulating pipe 13 is formed of an insulating ceramic (e.g., alumina), has a cylindrical tubular shape, and covers the circumference of the main body portion 11. The heater 14 is formed of tungsten and is embedded in the insulating pipe 13. Heater terminals 14a and 14b are formed on an end of the insulating pipe 13 on the back end side BE.

The electrode 20 includes a main body portion 21 and an insulating pipe 22. The main body portion 21 is a rod-shaped member formed of tungsten and extends in the axial direction DA. The insulating pipe 22 is formed of an insulating ceramic (e.g., alumina), has a cylindrical tubular shape, and covers the circumference of the main body portion 21, excluding opposite end portions of the main body portion 21.

The ion trapping section 30 includes a mixing/discharging member 31 and a cap member 32.

The mixing/discharging member 31 is a cylindrical tubular member formed of stainless steel and extends in the axial direction DA. The mixing/discharging member 31 has a gas flow passage 36 and a pipe insertion hole 37 formed therein.

The gas flow passage 36 is a through hole which penetrates the mixing/discharging member 31 in the axial direction DA and includes flow passages 36a, 36b, and 36c. The flow passage 36a is disposed at an end of the gas flow passage 36 on the forward end side FE, and is formed such that its opening area decreases from the forward end side FE toward the back end side BE. The flow passage 36b is disposed at an end of the gas flow passage 36 on the back end side BE and is formed such that its opening area increases from the forward end side FE toward the back end side BE. The flow passage 36c is disposed between the flow passage 36a and the flow passage 36b, and is formed such that it has a fixed opening area along the axial direction DA.

The pipe insertion hole 37 is a through hole which penetrates the mixing/discharging member 31 in the axial direction DA. The electrode 10 is inserted into the pipe insertion hole 37 in a state in which the inner circumferential wall of the pipe insertion hole 37 is in close contact with the circumference of the insulating pipe 13. As a result, the electrode 10 is disposed such that the curved portion 12 is located within the flow passage 36a.

Also, a through hole 38 is provided in the outer wall of the mixing/discharging member 31 to be located on the forward end side FE of the gas flow passage 36. The through hole 38 has an opening toward the downstream side of the exhaust pipe EP. This through hole 38 is the above-described gas discharge opening 38.

The cap member 32 is a circular plate member formed of stainless steel and is attached to the mixing/discharging member 31 so as to close the opening at an end of the mixing/discharging member 31 on the forward end side FE.

The exhaust gas electrification section 40 includes a nozzle member 41. The nozzle member 41 is a member formed of stainless steel, and extends in the axial direction DA. The nozzle member 41 is formed into the shape of a cylindrical tube having a bottom. The nozzle member 41 has an opening at its end on the forward end side FE and a bottom portion at its end on the back end side BE. The nozzle member 41 is fixed, with the end of the mixing/discharging member 31 on the back end side BE fitted into the opening of the nozzle member 41. A through hole 46 is provided in the bottom portion of the nozzle member 41. The through hole 46 is formed such that its opening area decreases from the back end side BE toward the forward end side FE. Hereinafter, the through hole 46 will be referred to as the nozzle 46. A through hole 47 is provided in the outer wall of the nozzle member 41. The through hole 47 has an opening toward the downstream side of the exhaust pipe EP. This through hole 47 is the above-described gas introduction opening 47.

The ion generation section 50 includes a pipe holder 51. The pipe holder 51 is a cylindrical tubular member formed of stainless steel and extends in the axial direction DA. The pipe holder 51 is fixed in a state in which an end of the nozzle member 41 on the back end side BE is fitted into an opening at an end portion of the pipe holder 51 on the forward end side FE. The pipe holder 51 has a through hole 56 (see FIG. 3), a through hole 57 (see FIG. 3), and a through hole 58 (see FIG. 4) which penetrate the pipe holder 51 in the axial direction DA. The main body portion 11 and the insulating pipe 13 of the electrode 10 are inserted into the through hole 56. The main body portion 21 and the insulating pipe 22 of the electrode 20 are inserted into the through hole 57. The through hole 58 is a flow passage through which high-pressure air from the pump 203 flows. The pipe holder 51 has an annular flange portion 59 extending radially outward from the circumference of the pipe holder 51.

Further, the particulate sensor 2 includes an inner tube 60 and a separator 70. The inner tube 60 is a cylindrical tubular member formed of stainless steel and extends in the axial direction DA. The inner tube 60 is fixed in a state in which an end of the pipe holder 51 on the back end side BE is fitted into an opening at an end of the inner tube 60 on the forward end side FE. The separator 70 is a cylindrical tubular insulating member extending in the axial direction DA, and is disposed inside the inner tube 60. The separator 70 has through holes 71, 72, 73, 74, and 75 which penetrate the separator 70 in the axial direction DA. Wires 161, 162, 163, and 164 which will be described below and which constitute the cable 160 are inserted into the through holes 71, 72, 73, and 74, respectively. The through hole 75 is a flow passage through which the high-pressure air from the pump 203 flows.

Notably, the inside metallic member 90 is composed of the mixing/discharging member 31, the cap member 32, the nozzle member 41, the pipe holder 51, and the inner tube 60.

Also, the outside metallic member 100 includes a metallic shell 110, a metallic plug member 120, and an outer tube 130.

The metallic shell 110 is a tubular member formed of stainless steel and extends in the axial direction DA. The metallic shell 110 has a main body portion 111, a flange portion 112, and a metallic member surrounding portion 113. The main body portion 111 has the form of a cylindrical tube extending in the axial direction DA and has an accommodation hole 111a which penetrates the main body portion 111 in the axial direction DA. The flange portion 112, which has a plate-like shape, extends radially outward from the circumference of an end of the main body portion 111 on the forward end side FE. The flange portion 112 has bolt through holes 112a which penetrate the flange portion 112 in the axial direction DA. Also, the flange portion 112 has an annular gasket holding groove 112b formed around the metallic member surrounding portion 113. The metallic member surrounding portion 113 has the form of a cylindrical tube extending in the axial direction DA and projects from the flange portion 112 toward the forward end side FE. The metallic member surrounding portion 113 projects in an axial direction such that its end is located on the forward end side FE of the gas introduction opening 47. Therefore, the metallic member surrounding portion 113 has a gas introduction window 113a at an axial position corresponding to the gas introduction opening 47. The gas introduction window 113a is formed by a U-shaped recess extending from the end of the metallic member surrounding portion 113.

The metallic plug member 120 is a tubular member formed of stainless steel and extends in the axial direction DA. The metallic plug member 120 has a main body portion 121, a forward end pressing portion 122, and a hexagonal portion 123. The main body portion 121 has the form of a cylindrical tube extending in the axial direction DA and has a male screw thread formed on the circumference thereof. The metallic plug member 120 and the metallic shell 110 are connected together when the male screw thread of the metallic plug member 120 is engaged with a female screw thread formed on the inner circumferential wall of the accommodation hole 111a of the metallic shell 110. The forward end pressing portion 122 has the form of a cylindrical tube having a diameter smaller than that of the main body portion 121 and projects in an axial direction toward the forward end side FE from an end of the main body portion 121 on the forward end side FE. The hexagonal portion 123 has the form of a plate which extends radially outward from the circumference of the main body portion 111 on the back end side BE and has a hexagonal peripheral shape.

The outer tube 130 is a cylindrical tubular member formed of stainless steel and extends in the axial direction DA. The outer tube 130 is fixed in a state in which an end of the metallic plug member 120 on the back end side BE is fitted into an opening at an end of the outer tube 130 on the forward end side FE.

Also, the particulate sensor 2 includes an insulating spacer 140, a plate packing 141, and an insulating spacer 150. The insulating spacer 140 is a cylindrical tubular member formed of alumina and extends in the axial direction DA. The insulating spacer 140 is disposed between the pipe holder 51 and the metallic shell 110 on the forward end side FE of the flange portion 59 of the pipe holder 51. As a result, the inside metallic member 90 and the outside metallic member 100 are electrically insulated from each other. An end of the insulating spacer 140 on the forward end side FE is exposed to the interior of the exhaust pipe EP when the particulate sensor 2 is attached to the exhaust pipe EP.

The plate packing 141 is an annular member and is disposed between the insulating spacer 140 and a step portion of the accommodation hole 111a of the metallic shell 110.

The insulating spacer 150 is a cylindrical tubular member formed of alumina and extends in the axial direction DA. The insulating spacer 150 is disposed between the pipe holder 51 and the metallic shell 110 on the back end side BE of the flange portion 59 of the pipe holder 51. As a result, the inside metallic member 90 and the outside metallic member 100 are electrically insulated from each other.

The cable 160 includes potential wires 161 and 162, heater wires 163 and 164, an air supply pipe 165, an insulating layer 166, a potential wire 167, an insulating layer 168, a ground potential wire 169, and an insulating layer 170.

The potential wires 161 and 162, the heater wires 163 and 164, and the air supply pipe 165 are disposed at the center of the cable 160. The insulating layer 166 is formed of resin and covers the circumferences of the wires 161 to 164 and the air supply pipe 165. The potential wire 167 is formed of braided thin copper wires and surrounds the circumference of the insulating layer 166. The insulating layer 168 is formed of resin and covers the circumference of the potential wire 167. The ground potential wire 169 is formed of braided thin copper wires and surrounds the circumference of the insulating layer 168. The insulating layer 170 is formed of resin and covers the circumference of the ground potential wire 169.

The potential wire 161 is connected to the main body portion 21 of the electrode 20. The potential wire 162 is connected to the main body portion 11 of the electrode 10. The heater wire 163 is connected to the heater terminal 14a through the heater connection terminal 173. The heater wire 164 is connected to the heater terminal 14b through the heater connection terminal 174. The air supply pipe 165 is connected to the air flow passage 204. The potential wire 167 is connected to the inner tube 60 by means of crimping. The ground potential wire 169 is connected to an end of the outer tube 130 on the back end side BE by means of crimping.

Also, the particulate sensor 2 includes a grommet 181 and a gasket 182. The grommet 181 is formed of insulating rubber to have a cylindrical tubular shape and is disposed between the cable 160 and the outer tube 130. The gasket 182 is an annular member formed of copper and is disposed in the gasket holding groove 112b of the flange portion 112. The particulate sensor 2 is fixed to the attachment portion EPA by inserting stud bolts EPB provided at the attachment portion EPA into the bolt through holes 112a of the flange portion 112 and fastening the stud bolts EPB by nuts EPN. When the particulate sensor 2 is fixed to the attachment portion EPA, the gasket 182 comes into close contact with the attachment portion EPA and the metallic shell 110, whereby the airtightness between the particulate sensor 2 and the exhaust pipe EP is secured.

Next, operation of the particulate sensor 2 for detecting the amount of particulates contained in exhaust gas will be described.

Figure 6:
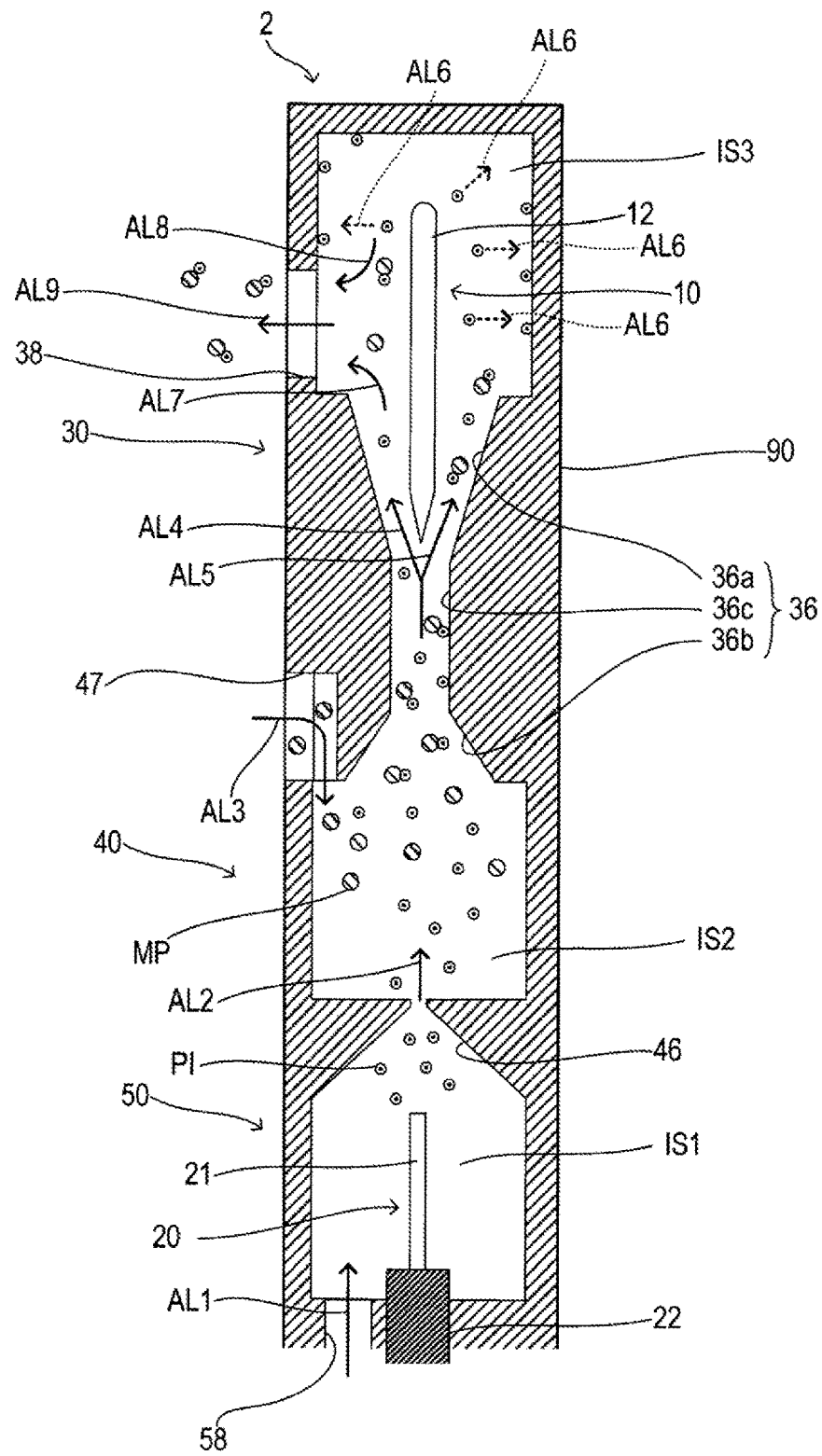
FIG. 6 is a schematic view illustrating the detection operation of the particulate sensor 2.

As shown in FIG. 6, the particulate sensor 2 generates positive ions PI at the ion generation section 50. Specifically, when a voltage is applied to the particulate sensor 2 by the circuit section 202 such that the electrode 20 becomes a positive electrode and the nozzle 46 becomes a negative electrode, corona discharge occurs between the electrode 20 and the nozzle 46. As a result of this corona discharge, the positive ions PI are generated at the ion generation section 50.

The positive ions PI generated at the ion generation section 50 are jetted from the nozzle 46 into an internal space IS2 of the exhaust gas electrification section 40 (see an arrow AL2) together with high-pressure air (see an arrow AL1) supplied to an internal space IS1 of the ion generation section 50 through the through hole 58. When air containing the positive ions PI is jetted from the nozzle 46 into the internal space IS2, a negative pressure is created in the internal space IS2, and exhaust gas containing particulates MP is taken or introduced into the internal space IS2 through the gas introduction opening 47 (see an arrow AL3).

As a result, the air jetted from the nozzle 46 and the exhaust gas introduced through the gas introduction opening 47 are mixed together within the internal space IS2, whereby the positive ions PI within the air attach to the particulates MP within the exhaust gas.

The exhaust gas mixed with the air within the internal space IS2 passes through the gas flow passage 36 formed in the ion trapping section 30, and flows into an internal space IS3 of the ion trapping section 30 (see arrows AL4 and AL5).

The curved portion 12 of the electrode 10 is disposed along the flow direction of the exhaust gas so as to extend from the flow passage 36a of the gas flow passage 36 to the internal space IS3. A voltage is applied to the particulate sensor 2 by the circuit section 202 such that the electrode 10 becomes a positive electrode and the inside metallic member 90 becomes a negative electrode. As a result, the positive ions PI having failed to attach to the particulates MP within the exhaust gas move in a direction away from the curved portion 12 of the electrode 10 due to repulsive forces generated between the positive ions PI and the curved portion 12 of the electrode 10 (see an arrow AL6). The positive ions PI moving in the direction away from the curved portion 12 are trapped by the inner wall of the inside metallic member 90 serving as a negative electrode. As a result, a current corresponding to the amount of the positive ions PI trapped by the inner wall of the inside metallic member 90 flows through the inside metallic member 90. Meanwhile, since the particulates MP electrified as a result of attachment of the positive ions PI thereto are greater in mass than the positive ions PI, the influence of the repulsive forces generated between the electrified particulates MP and the curved portion 12 of the electrode 10 is small. Therefore, the electrified particulates MP follow the flow of the exhaust gas (see arrows AL7 and AL8), and are discharged from the gas discharge opening 38 (see an arrow AL9).

Next, a method of detecting the amount of particulates within the exhaust gas will be described.

Figure 7:
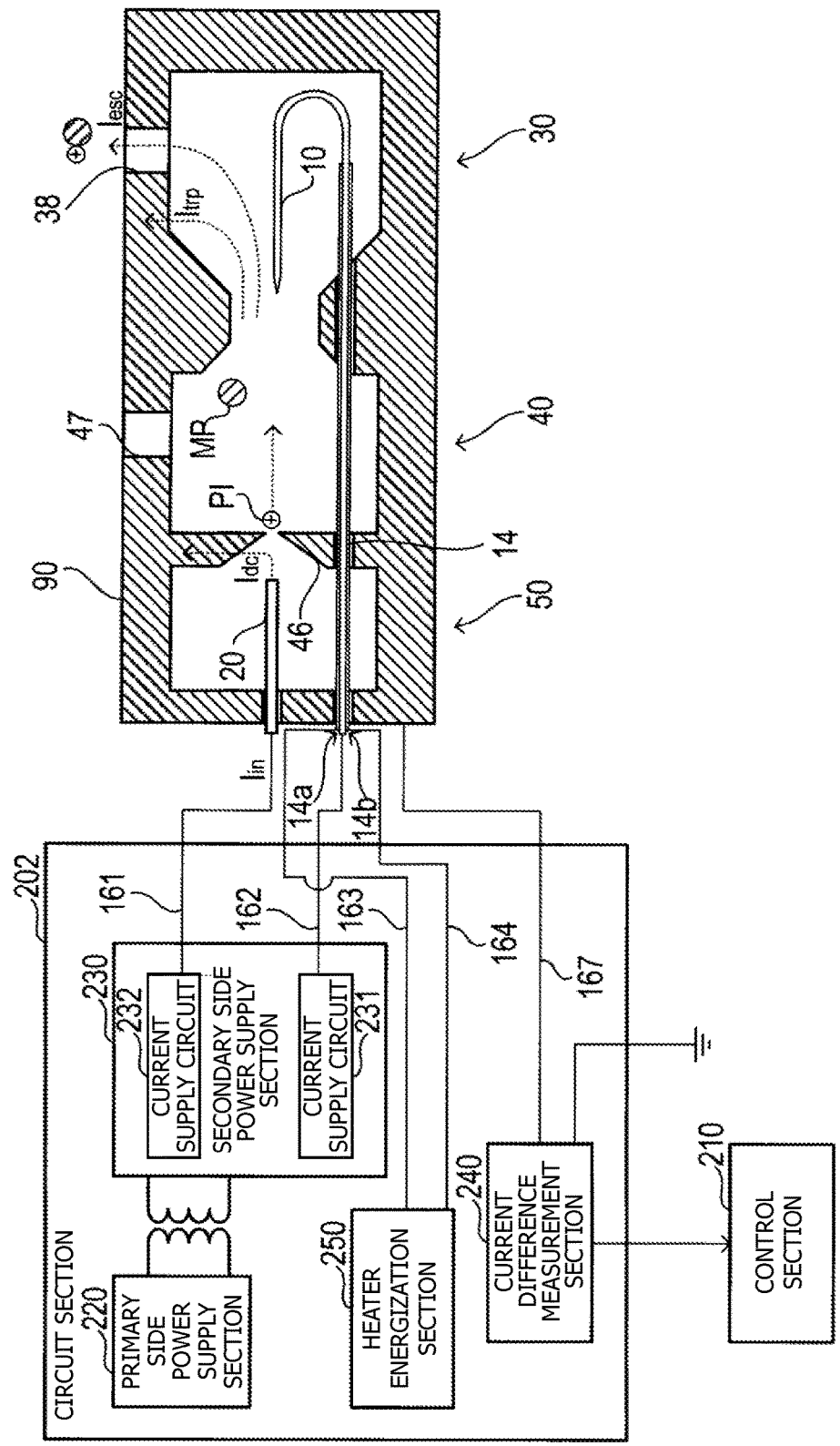
FIG. 7 is a schematic diagram illustrating a method of detecting the amount of particulates.

As shown in FIG. 7, the circuit section 202 includes a primary side power supply section 220, a secondary side power supply section 230, a current difference measurement section 240, and a heater energization section 250. The primary side power supply section 220 supplies high voltage electric power to the secondary side power supply section 230 in accordance with an instruction from the control section 210. The secondary side power supply section 230 includes current supply circuits 231 and 232.

The current supply circuit 231 is connected to the electrode 10 through the potential wire 162. As a result, the particulate sensor 2 receives electric power for trapping the positive ions PI from the current supply circuit 231.

The current supply circuit 232 is connected to the electrode 20 through the potential wire 161. As a result, the particulate sensor 2 receives electric power for generating the positive ions PI from the current supply circuit 232 by means of corona discharge. The current supply circuit 232 is a constant current circuit and supplies a constant input current Iin of, for example, about 5 µA to the electrode 20.

The current difference measurement section 240 is a circuit for measuring escaped current Iesc which will be described below and is electrically connected to the inside metallic member 90 through the potential wire 167. Notably, the inside metallic member 90 is held within the exhaust pipe EP in a state in which it is insulated from the exhaust pipe EP maintained at the second potential (the ground potential). Also, the current difference measurement section 240 is grounded through the exhaust pipe EP or the chassis of the vehicle.

The heater energization section 250 is a circuit for supplying electric current to the heater 14 by PWM (pulse-width-modulation) control to thereby cause the heater 14 to generate heat. The heater energization section 250 is connected to the heater terminal 14a through the heater wire 163 and is connected to the heater terminal 14b through the heater wire 164.

When a current flows from the current supply circuit 232 to the electrode 20, as a result of corona discharge, a discharge current Idc flows from the electrode 20 to the inside metallic member 90 through the nozzle 46, whereby the positive ions PI are generated. As described above, some of the positive ions PI attach to the particulates MP to thereby produce electrified particulates, and are discharged to the outside of the particulate sensor 2 through the gas discharge opening 38 together with the particulates MP (in other words, in the form of electrified particulates). Meanwhile, the remaining positive ions PI having failed to attach to the particulates MP are trapped by the inside metallic member 90.

When a current corresponding to the flow of the positive ions PI discharged to the outside of the particulate sensor 2 is defined as escaped current Iesc, and a current corresponding to the flow of the positive ions PI trapped by the inside metallic member 90 is defined as trapped current Itrp, a relation represented by the following expression (1) holds.

$$Iin=Idc+Itrp+Iesc \tag{1}$$

The discharge current Idc and the trapped current Itrp flow to the inside metallic member 90, and the input current Iin is maintained at a constant value. Therefore, as shown in the following expression (2), the escaped current Iesc can be calculated from the difference between the input current Iin and the sum of the discharge current Idc and the trapped current Itrp.

$$Iesc=Iin-(Idc+Itrp) \tag{2}$$

As shown in the expression (2), a current of the input current Iin minus the escaped current Iesc flows in the inside metallic member 90. Therefore, the reference potential of the inside metallic member 90 becomes lower than the external reference potential. As a result of a decrease in the potential of the inside metallic member 90, a compensation current Ic for compensating the potential decrease flows from the current difference measurement section 240 to the inside metallic member 90 through the potential wire 167. This compensation current Ic corresponds to the escaped current Iesc. In other words, the compensation current Ic (the escaped current Iesc) corresponds to a signal current which flows between the first potential and the second potential (the ground potential) in proportion to the amount of electrified particulates. The current difference measurement section 240 measures the value of the compensation current Ic, and uses the measured value of the compensation current Ic as a measured value of the escaped current Iesc. The current difference measurement section 240 outputs an escaped current signal representing the measured value of the escaped current Iesc to the control section 210.

The control section 210 specifies the measured value of the escaped current Iesc (the signal current flowing between the first potential and the second potential in proportion to the amount of the electrified particulates) based on the escaped current signal input from the current difference measurement section 240, and calculates the amount of the particulates within the exhaust gas through use of, for example, a map or a computation expression which shows the relation between the measured value of the escaped current Iesc and the amount of the particulates within the exhaust gas.

Also, the CPU 211 of the control section 210 executes regulator control processing.

Here, the steps of the regulator control processing will be described. This regulator control processing is processing which is started immediately after the control section 210 begins its operation.

Figure 8:
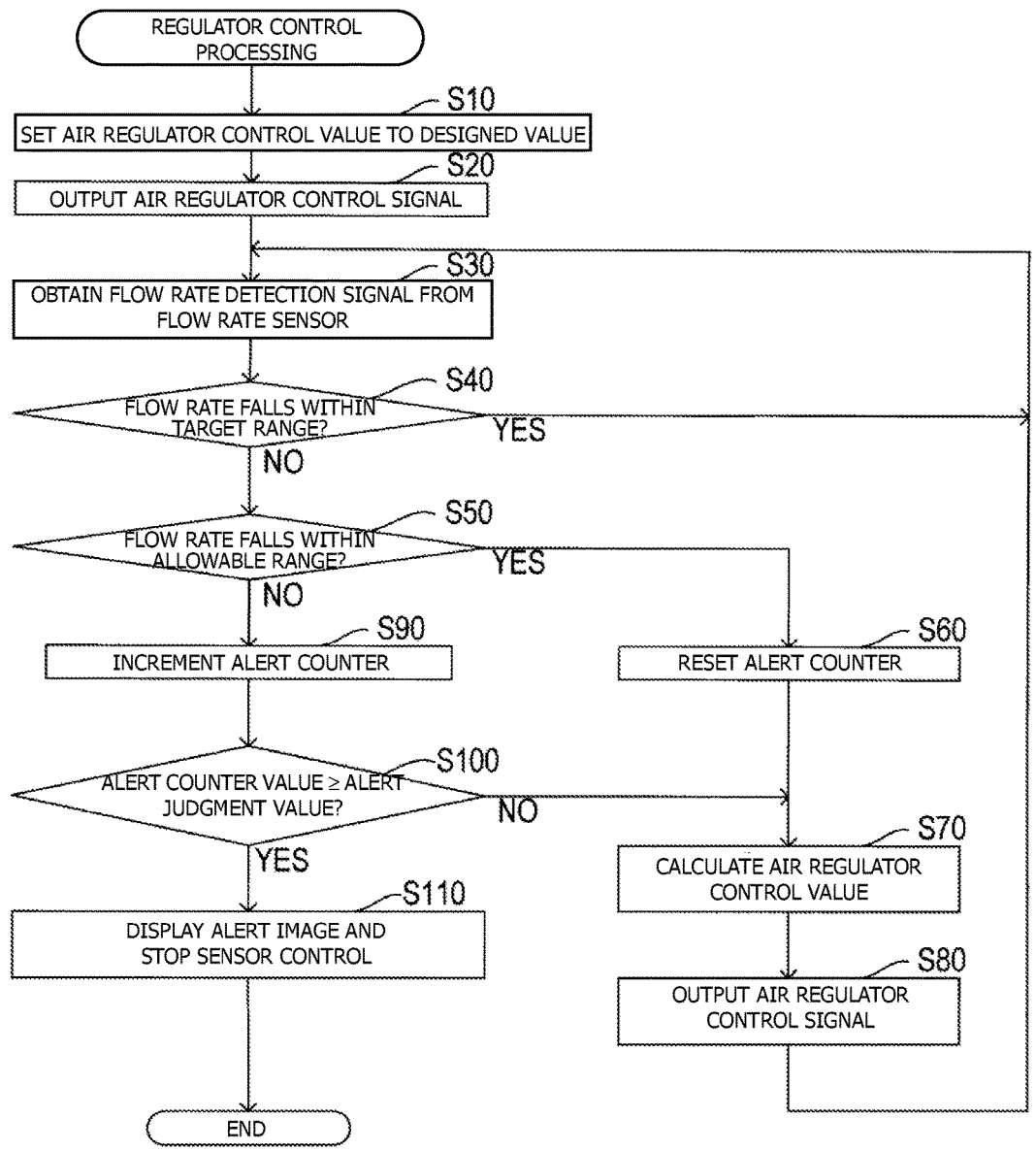
FIG. 8 is a flowchart showing regulator control processing.

When this regulator control processing is executed, as shown in FIG. 8, the CPU 211 of the control section 210 first sets an air regulator control value provided in the RAM 213 to a designed value in S10. The designed value is a value which is set in advance in a process of manufacturing the particulate detection apparatus 3 such that the flow rate of the high-pressure air flowing through the air flow passage 204 coincides with a target value set in advance.

Subsequently, in S20, the CPU 211 outputs to the air regulator 205 an air regulator control signal indicating the air regulator control value set in S10.

Next, in S30, the CPU 211 obtains a flow rate detection signal from the flow rate sensor 207. Subsequently, in S40, the CPU 211 determines whether or not the flow rate indicated by the flow rate detection signal falls within a target range set in advance. The target range is a range which contains the above-mentioned target value. In the case where the flow rate falls within the target range (S40: YES), the CPU 211 proceeds to S30.

Meanwhile, in the case where the flow rate falls outside the target range (S40: NO), in S50, the CPU 211 determines whether or not the flow rate falls within an allowable range set in advance. The allowable range is a range set to contain the entire target range.

In the case where the flow rate falls within the allowable range (S50: YES), the CPU 211 in S60 resets (sets to zero) an alert counter provided in the RAM 213. Further, in S70, the CPU 211 calculates an air regulator control value so that the flow rate coincides with the target value based on the flow rate indicated by the flow rate detection signal and the air regulator control value at the present point in time. Subsequently, in S80, the CPU 211 outputs to the air regulator 205 the air regulator control signal indicating the air regulator control value calculated in S70. The CPU 211 then proceeds to S30.

Meanwhile, in the case where the flow rate falls outside the allowable range (S50: NO), in S90, the CPU 211 increments (adds 1 to) the alert counter. Subsequently, in S100, the CPU 211 determines whether or not the value of the alert counter is equal to or greater than an alert judgment value (in the present embodiment, a value corresponding to, for example, 10 seconds) set in advance. In the case where the value of the alert counter is less than the alert judgment value (S100: NO), the CPU 211 proceeds to S70. Meanwhile, in the case where the value of the alert counter is equal to or greater than the alert judgment value (S100: YES), in S110, the CPU 211 causes the display section 208 to display an alert image indicating that an anomaly has occurred in the supply of the high-pressure air, stops the control of the particulate sensor 2, and ends the regulator control processing.

The particulate detection apparatus 3 configured as described above includes the pump 203 for supplying air to the particulate sensor 2 which detects the amount of particulates contained in exhaust gas, and controls the particulate sensor 2.

The particulate detection apparatus 3 includes the air regulator 205 which adjusts the flow rate of the air supplied from the pump 203 to the particulate sensor 2. The particulate detection apparatus 3 detects the flow rate of the air supplied from the pump 203 to the particulate sensor 2 through use of the flow rate sensor 207 (S30). The particulate detection apparatus 3 controls the air regulator 205 based on the result of the detection by the flow rate sensor 207 so as to maintain the flow rate of the air at the target value set in advance, to thereby maintain the detection accuracy of the particulate sensor 2 at a constant level (S40, S50, S70, S80).

As described above, the particulate detection apparatus 3 maintains the detection accuracy in detecting the amount of particulates by the particulate sensor 2 at a constant level by detecting the flow rate which correlates with the amount of air suppled to the particulate sensor 2. In other words, the particulate detection apparatus 3 maintains a consistent particulate amount detection accuracy that has been set in advance (set at the shipment time of a product) by using the detected flow rate which correlates with the amount of air supplied to the particulate sensor 2. Therefore, the particulate detection apparatus 3 can suppress a decrease in the detection accuracy due to a change in the amount of air supplied to the particulate sensor 2, to thereby improve the detection accuracy of the particulate sensor 2.

Also, in the case where a state in which the flow rate of the air falls outside the allowable range set in advance continues for at least a time corresponding to the alert judgment value set in advance, the particulate detection apparatus 3 displays an alert image indicating that an anomaly has occurred in the supply of the high-pressure air (S100, S110). As a result, the particulate detection apparatus 3 can alert a user of the particulate detection apparatus 3 to the occurrence of the anomaly; i.e., the continuation of a state in which the flow rate of the air falls outside the allowable range. Therefore, the particulate detection apparatus 3 can restrain the continuation of the state in which the detection accuracy of the particulate sensor 2 has decreased due to a change in the amount of the air, to thereby improve the detection accuracy of the particulate sensor 2.

In the above-described embodiment, the pump 203 corresponds to the gas supply section of the present invention; the flow rate sensor 207 and the processing of S30 correspond to the gas detection means of the present invention; the processing of S40, S50, S70, and S80 corresponds to the maintenance means of the present invention; the air regulator 205 corresponds to the adjustment means of the present invention; the processing of S100 and S110 corresponds to the warning means of the present invention; the circuit section 202 containing the current supply circuit 231 corresponds to the power supply means of the present invention; a portion of the particulate sensor 2 which contains the exhaust gas electrification section 40 and is exposed to the interior of the exhaust pipe EP corresponds to the detection section of the present invention; and the ion generation section 50 and the nozzle 46 corresponds to the gas jetting source of the present invention.

(Second Embodiment)

A second embodiment of the present invention will now be described with reference to FIGS. 9 and 10. Notably, in the description of the second embodiment, mainly portions different from those of the first embodiment will be described.

Figure 9:
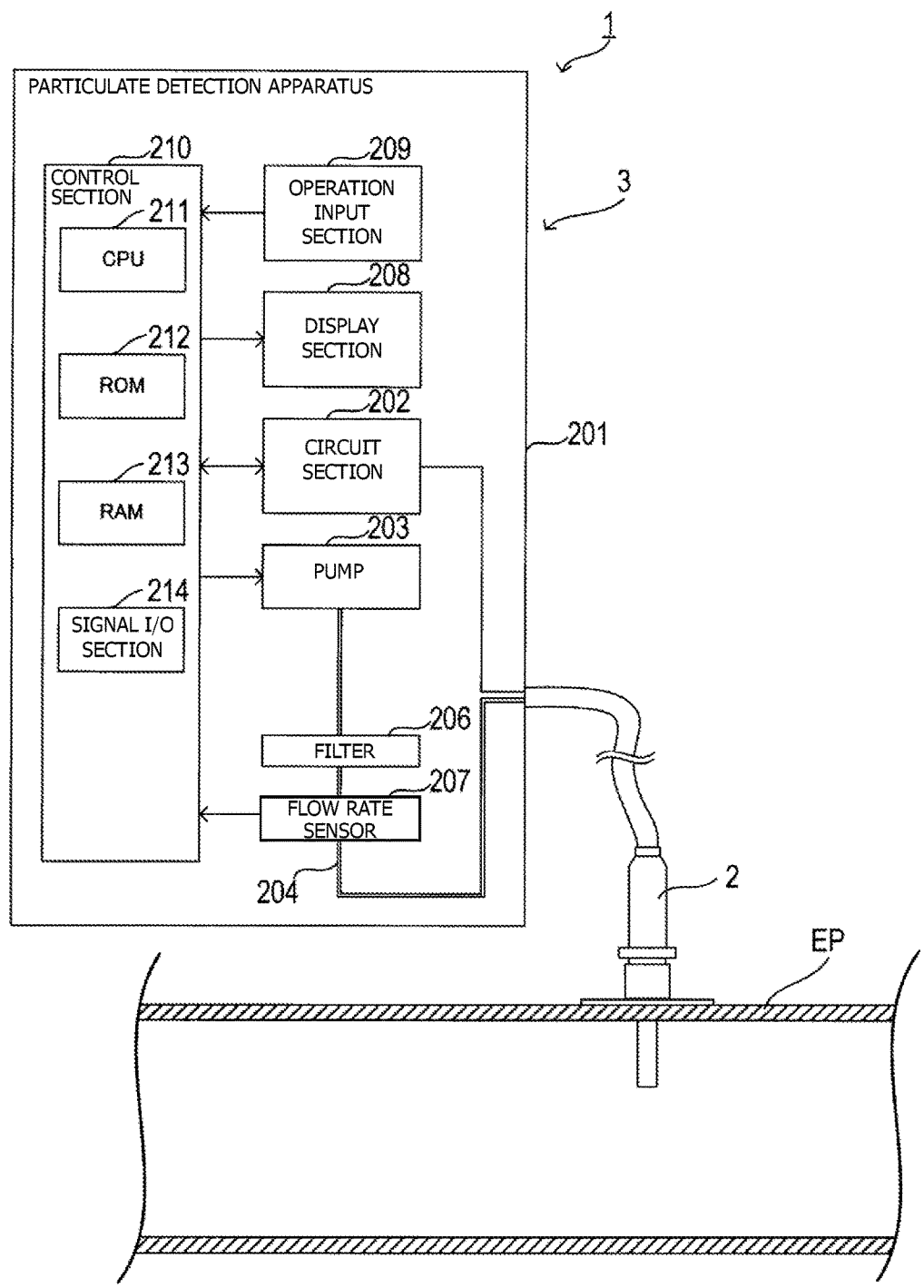
FIG. 9 is a diagram schematically showing the configuration of a particulate detection system 1 of a second embodiment.

As shown in FIG. 9, a particulate detection system 1 of the second embodiment differs from the particulate detection system 1 of the first embodiment in that the air regulator 205 is omitted.

Also, the particulate detection system 1 of the second embodiment differs from the particulate detection system 1 of the first embodiment in that the CPU 211 of the control section 210 executes particulate amount correction processing instead of the regulator control processing.

The steps of the particulate amount correction processing will now be described. This particulate amount correction processing begins immediately after the control section 210 starts its operation.

Figure 10:
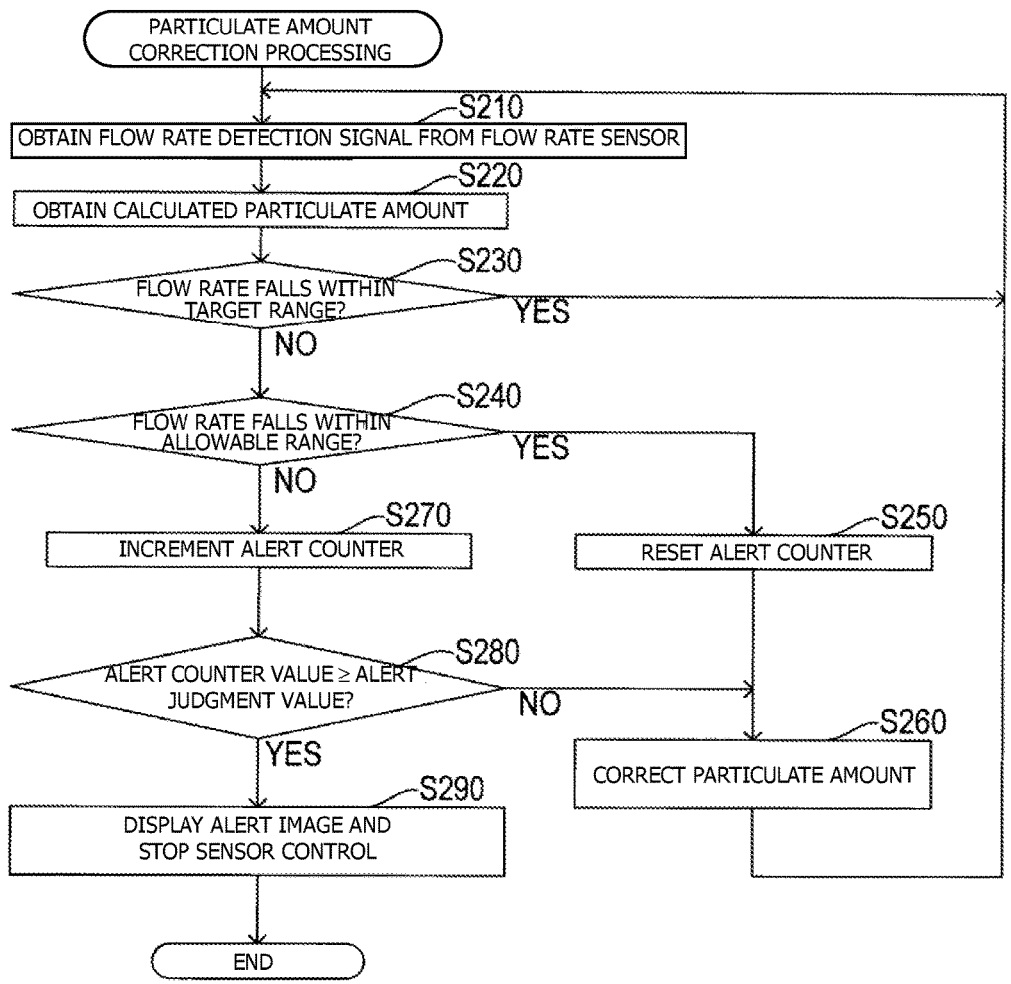
FIG. 10 is a flowchart showing particulate amount correction processing.

When this particulate amount correction processing is executed, as shown in FIG. 10, the CPU 211 of the control section 210 first obtains a flow rate detection signal from the flow rate sensor 207 in S210. Further, in S220, the CPU 211 obtains the amount of particulates calculated by the control section 210 based on the measured value of the escaped current Iesc.

Subsequently, in S230, the CPU 211 determines whether or not the flow rate indicated by the flow rate detection signal falls within the target range set in advance. In the case where the flow rate falls within the target range (S230: YES), the CPU 211 proceeds to S210.

Meanwhile, in the case where the flow rate falls outside the target range (S230: NO), in S240, the CPU 211 determines whether or not the flow rate falls within the allowable range set in advance. In the case where the flow rate falls within the allowable range (S240: YES), in S250, the CPU 211 resets the alert counter provided in the RAM 213. Further, in S260, the CPU 211 corrects the amount of particulates by referring to a three-dimensional map in which corrected values of the amount of particulates are set in advance, while using, as parameters, the flow rate indicated by the flow rate detection signal obtained in S210 and the amount of particulates obtained in S220. The CPU 211 then proceeds to S210.

Meanwhile, in the case where the flow rate falls outside the allowable range (S240: NO), in S270, the CPU 211 increments the alert counter. Subsequently, in S280, the CPU 211 determines whether or not the value of the alert counter is equal to or greater than the alert judgment value set in advance. In the case where the value of the alert counter is less than the alert judgment value (S280: NO), the CPU 211 proceeds to S260. Meanwhile, in the case where the value of the alert counter is equal to or greater than the alert judgment value (S280: YES), in S290, the CPU 211 causes the display section 208 to display an alert image indicating that an anomaly has occurred in the supply of the high-pressure air, stops the control of the particulate sensor 2, and ends the particulate amount correction processing.

The particulate detection apparatus 3 configured as described above detects the flow rate of the air supplied from the pump 203 to the particulate sensor 2 using the flow rate sensor 207 (S210). The particulate detection apparatus 3 maintains the detection accuracy of the particulate sensor 2 at a constant level by correcting the amount of particulates, which is calculated from the measured value of the escaped current Iesc, based on the result of the detection by the flow rate sensor 207 (S220, S230, S260).

As described above, the particulate detection apparatus 3 maintains the detection accuracy in detecting the amount of particulates by the particulate sensor 2 at a constant level by detecting the flow rate which correlates with the amount of the air suppled to the particulate sensor 2. Therefore, the particulate detection apparatus 3 can suppress a decrease in detection accuracy due to a change in the amount of air supplied to the particulate sensor 2, to thereby improve the detection accuracy of the particulate sensor 2.

Also, in the case where a state in which the flow rate of the air falls outside the allowable range set in advance continues for at least a time corresponding to the alert judgment value set in advance, the particulate detection apparatus 3 displays an alert image indicating that an anomaly has occurred in the supply of the high-pressure air (S280, S290). As a result, the particulate detection apparatus 3 can alert a user of the particulate detection apparatus 3 to the occurrence of the anomaly; i.e., the continuation of the state in which the flow rate of the air does not coincide with the target value. Therefore, the particulate detection apparatus 3 can prevent the continuation of a state in which the detection accuracy of the particulate sensor 2 has decreased due to a change in the amount of the air, to thereby improve the detection accuracy of the particulate sensor 2.

In the above-described embodiment, the flow rate sensor 207 and the processing of S210 correspond to the gas detection means of the present invention; the processing of S220, S230, and S260 corresponds to the maintenance means of the present invention; and the processing of S280 and S290 corresponds to the warning means of the present invention.

(Third Embodiment)

A third embodiment of the present invention will now be described with reference to FIGS. 11 and 12. Notably, in the description of the third embodiment, mainly portions different from those of the first embodiment will be described.

Figure 11:
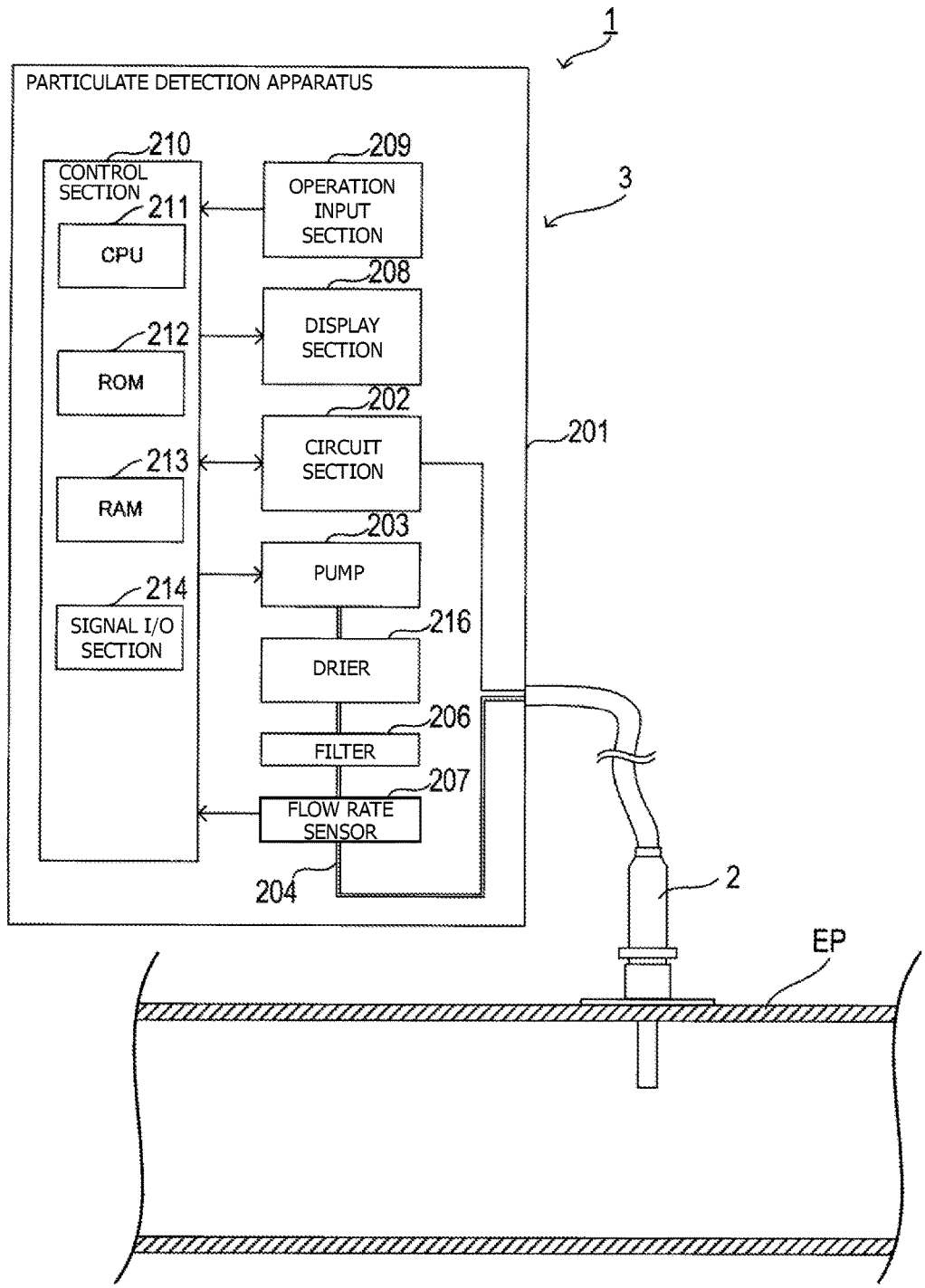
FIG. 11 is a diagram schematically showing the configuration of a particulate detection system 1 of a third embodiment.

As shown in FIG. 11, a particulate detection system 1 of the third embodiment differs from the particulate detection system 1 of the first embodiment in that the air regulator 205 is omitted, and a drier 216 is added.

Also, the particulate detection system 1 of the third embodiment differs from the particulate detection system 1 of the first embodiment in that the CPU 211 of the control section 210 executes pump control processing instead of the regulator control processing.

The drier 216 adjusts the humidity of the high-pressure air supplied from the pump 203 through the air flow passage 204. The drier 216 of the present embodiment is a known hollow-fiber-membrane-type drier which includes a hollow fiber membrane formed of, for example, fluororesin. The drier adjusts the humidity of the air introduced into the interior of the hollow fiber membrane by discharging, to the outside of the hollow fiber membrane, moisture contained in the air introduced into the interior of the hollow fiber membrane. The drier 216 is disposed in the air flow passage 204 so as to be located between the pump 203 and the flow rate sensor 207.

The pump 203 adjusts the flow rate of the produced high-pressure air by changing its rotational speed in accordance with a pump control value indicated by a pump control signal input from the control section 210. In the present embodiment, the pump control signal is a PWM (pulse-width modulation) signal.

The steps of the pump control processing will now be described. This pump control processing is processing which begins immediately after the control section 210 starts its operation.

Figure 12:
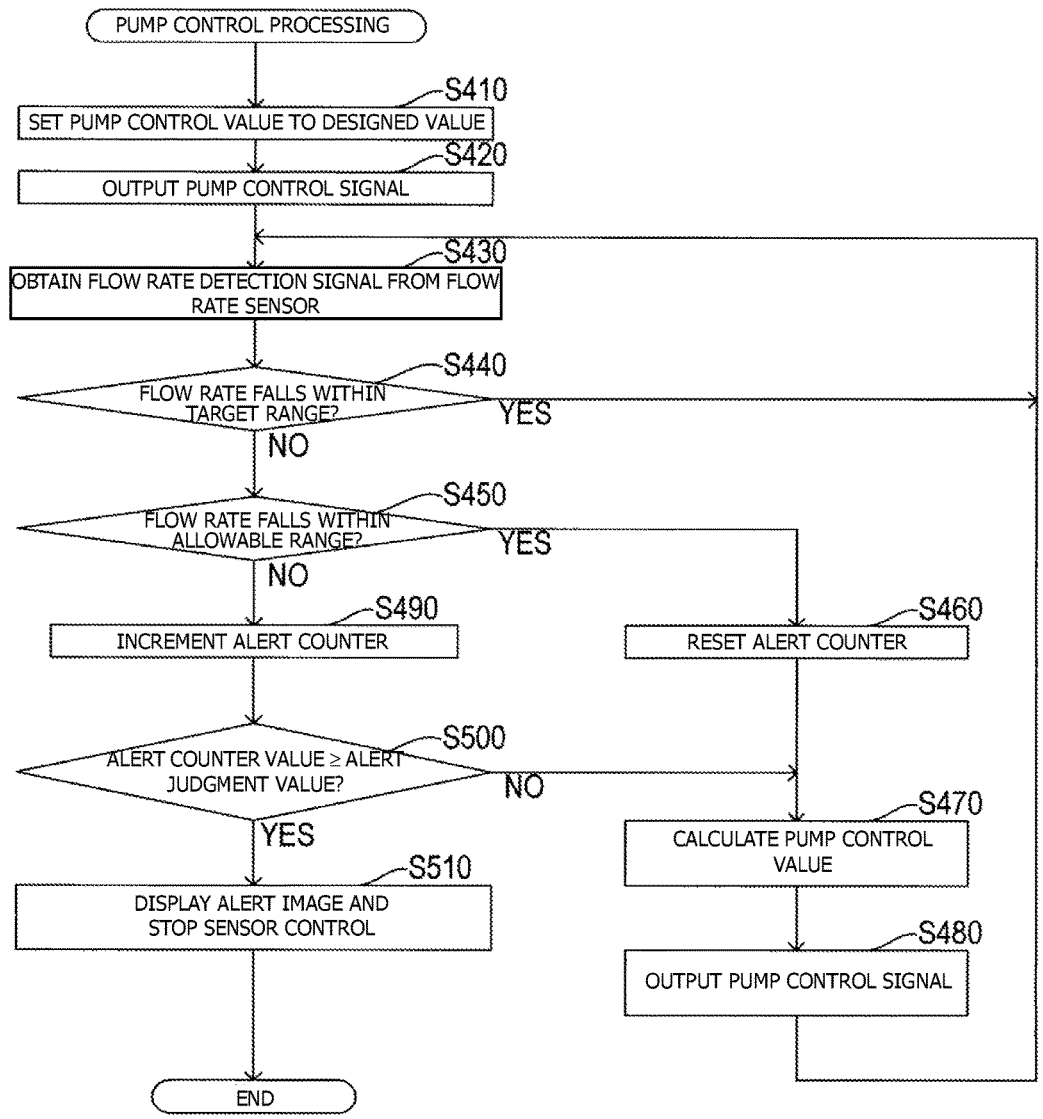
FIG. 12 is a flowchart showing pump control processing.

When this pump control processing is executed, as shown in FIG. 12, the CPU 211 of the control section 210 first sets a pump control value provided in the RAM 213 to a designed value in S410. The designed value is a value which is set in advance in the process of manufacturing the particulate detection apparatus 3 such that the flow rate of the high-pressure air flowing through the air flow passage 204 coincides with a target value set in advance.

Subsequently, in S420, the CPU 211 outputs to the pump 203 a pump control signal indicating the pump control value set in S410.

Next, in S430, the CPU 211 obtains the flow rate detection signal from the flow rate sensor 207. Subsequently, in S440, the CPU 211 determines whether or not the flow rate indicated by the flow rate detection signal falls within the target range set in advance. The target range is a range which contains the above-mentioned target value. In the case where the flow rate falls within the target range (S440: YES), the CPU 211 proceeds to S430.

Meanwhile, in the case where the flow rate falls outside the target range (S440: NO), in S450, the CPU 211 determines whether or not the flow rate falls within the allowable range set in advance. The allowable range is a range set to contain the entire target range.

In the case where the flow rate falls within the allowable range (S450: YES), the CPU 211 in S460 resets (sets to zero) the alert counter provided in the RAM 213. Further, in S470, the CPU 211 calculates a pump control value so that the flow rate coincides with the target value based on the flow rate indicated by the flow rate detection signal and the pump control value at the present point in time. Subsequently, in S480, the CPU 211 outputs to the pump 203 the pump control signal indicating the pump control value calculated in S470. The CPU 211 then proceeds to S430.

Meanwhile, in the case where the flow rate falls outside the allowable range (S450: NO), in S490, the CPU 211 increments (adds 1 to) the alert counter. Subsequently, in S500, the CPU 211 determines whether or not the value of the alert counter is equal to or greater than an alert judgment value (in the present embodiment, a value corresponding to, for example, 10 seconds) set in advance. In the case where the value of the alert counter is less than the alert judgment value (S500: NO), the CPU 211 proceeds to S470. Meanwhile, in the case where the value of the alert counter is equal to or greater than the alert judgment value (S500: YES), in S510, the CPU 211 causes the display section 208 to display an alert image indicating that an anomaly has occurred in the supply of the high-pressure air, stops the control of the particulate sensor 2, and ends the pump control processing.

The particulate detection apparatus 3 configured as described above detects the flow rate of the air supplied from the pump 203 to the particulate sensor 2 through use of the flow rate sensor 207 (S430). The particulate detection apparatus 3 maintains the flow rate of the air at the target value set in advance by controlling the pump 203 based on the result of the detection by the flow rate sensor 207, whereby the particulate detection apparatus 3 maintains the detection accuracy of the particulate sensor 2 at a constant level (S440, S450, S470, S480).

As described above, the particulate detection apparatus 3 maintains the accuracy in detecting the amount of particulates by the particulate sensor 2 at a constant level by detecting the flow rate which correlates with the amount of air supplied to the particulate sensor 2. Therefore, the particulate detection apparatus 3 can prevent a decrease in detection accuracy due to a change in the amount of the air supplied to the particulate sensor 2, to thereby improve the detection accuracy of the particulate sensor 2.

Also, the particulate detection apparatus 3 includes the drier 216 which adjusts the humidity of the air supplied from the pump 203 and flowing through the air flow passage 204. As a result, the particulate detection apparatus 3 can restrain a change in the detection accuracy of the particulate sensor 2 due to a change in the humidity of the air.

Also, in particulate detection apparatus 3, the drier 216 is disposed in the air flow passage 204 so as to be located between the pump 203 and the flow rate sensor 207. Therefore, even when the flow rate of the air changes as a result of passage of the air through the drier 216, the particulate detection apparatus 3 can detect such a change through use of the flow rate sensor 207. Therefore, the particulate detection apparatus 3 can prevent a decrease in detection accuracy due to the above-described change generated as a result of passage of the air through the drier 216, to thereby improve the detection accuracy of the particulate sensor 2.

Also, in the particulate detection apparatus 3, the particulate sensor 2 is a direct-insertion-type sensor which is inserted directly into the exhaust pipe EP of the internal combustion engine so as to detect the amount of particulates contained in exhaust gas within the exhaust pipe EP. The particulate detection apparatus 3 is connected to the particulate sensor 2 through the air flow passage 204 through which the air supplied from the pump 203 flows. As a result, the particulate detection apparatus 3 can detect the amount of particulates contained in the exhaust gas without introducing exhaust gas into the interior of the particulate detection apparatus 3.

In the above-described embodiment, the processing of S440, S450, S470, and S480 corresponds to the maintenance means of the present invention; the air flow passage 204 corresponds to the gas flow passage of the present invention; and the drier 216 corresponds to the humidity adjustment section of the present invention.

Although embodiments of the present invention have been described, the present invention is not limited to the above-described embodiments and may be implemented in various forms without departing from the technical scope of the present invention.

For example, in the above-described embodiments, the flow rate of the high-pressure air flowing through the air flow passage 204 is detected by the flow rate sensor 207. However, instead of detecting the flow rate, the pressure of the high-pressure air flowing through the air flow passage 204 may be detected by a pressure sensor. Also, both the flow rate and pressure of the high-pressure air may be detected. Further, the means employed by the particulate sensor so as to detect the amount of particulates is not limited to generating ions by using corona discharge and detecting the amount of particulates by using the ions, so long as the amount of particulates is detected through supply of a gas to the detection section into which a gas under measurement is introduced. Also, in the above-described embodiments, high-pressure air is supplied by the pump 203. However, the gas supplied by the pump 203 is not limited to air, and a gas whose composition differs from that of air may be supplied.

In the above-described embodiments, the particulate detection apparatus includes the filter 206 for removing dust, etc., contained in the high-pressure air flowing through the air flow passage 204, and the filter 206 may be contaminated as a result of long term use. In such a case, the amount of air supplied to the particulate sensor 2 changes. However, through application of the present invention (the above-described embodiments), the particulate amount detection accuracy can be maintained at a constant level even when the filter is contaminated with elapse of time.

In the above-described third embodiment, the humidity of the air is adjusted by removing moisture contained in the air by using the drier 216 (i.e., by dehumidification). However, moisture may be added to the air so as to adjust the humidity of the air. Also, in the above-described embodiments, the particulate sensor 2 is inserted directly into the exhaust pipe EP of the internal combustion engine. However, a tubular gas flow pipe may be separately attached (connected) to the outlet side of the exhaust pipe EP, and the particulate sensor 2 may be inserted directly into the gas flow pipe so as to detect the amount of particulates. Further, in the above-described embodiments, the particulate sensor 2 is a direct-insertion-type sensor. However, the particulate sensor 2 may have a structure different from that of a direct-insertion-type sensor. Specifically, in such a structure, the particulate sensor 2 is provided at a position (location) separated from the exhaust pipe EP, a sampling passage for sampling the exhaust gas flowing through the exhaust pipe EP and leading the sampled exhaust gas to the particulate sensor 2 is attached to the exhaust pipe EP at the midpoint thereof, and the particulate sensor 2 detects the amount of particulates contained in the sampled exhaust gas.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application Nos. 2015-135444 filed Jul. 6, 2015 and 2016-060269 filed Mar. 24, 2016, the above-noted applications incorporated herein by reference in their entirety.

What is claimed is:

1. A particulate detection apparatus which controls a particulate sensor for detecting an amount of particulates contained in a gas under measurement and which includes a gas supply section for supplying a gas different from the gas under measurement to a detection section of the particulate sensor into which the gas under measurement is introduced, comprising:
   gas detection means for detecting at least one of flow rate and pressure of the gas supplied from the gas supply section to the particulate sensor; and
   maintenance means for maintaining, based on the result of the detection by the gas detection means, a desired accuracy in detecting the amount of particulates by the particulate sensor.

2. The particulate detection apparatus as claimed in claim 1, further comprising:
   adjustment means for adjusting the at least one of the flow rate and pressure of the gas supplied from the gas supply section to the particulate sensor,
   wherein the maintenance means controls the adjustment means based on the result of the detection by the gas detection means so as to maintain the at least one of the flow rate and pressure of the gas at a target value set in advance.

3. The particulate detection apparatus as claimed in claim 1, wherein the maintenance means maintains the detection accuracy by correcting the result of the detection by the particulate sensor based on the result of the detection by the gas detection means.

4. The particulate detection apparatus as claimed in claim 1, wherein the maintenance means controls the gas supply section based on the result of the detection by the gas detection means so as to maintain the at least one of the flow rate and pressure of the gas at a target value set in advance.

5. The particulate detection apparatus as claimed in claim 1, further comprising warning means for issuing a warning when a state, in which at least one of the flow rate and pressure of the gas falls outside an allowable range set in advance, continues for at least a warning judgment time set in advance.

6. The particulate detection apparatus as claimed in claim 1, further comprising a humidity adjustment section for adjusting humidity of the gas supplied from the gas supply section and flowing through a gas flow passage.

7. The particulate detection apparatus as claimed in claim 6, wherein the humidity adjustment section is disposed in the gas flow passage, the gas flow passage being located between the gas supply section and the gas detection means.

8. The particulate detection apparatus as claimed in claim 1, wherein
   the particulate sensor includes a gas jetting source which generates ions by means of corona discharge and jets the generated ions into the detection section together with the gas supplied from the gas supply section; and
   the particulate detection apparatus includes power supply means for supplying electric power for producing the corona discharge.

9. The particulate detection apparatus as claimed in claim 1, wherein
   the particulate sensor is a direct-insertion sensor which is inserted directly into an exhaust pipe through which exhaust gas discharged from an internal combustion engine flows, or into a gas flow pipe attached to an outlet side of the exhaust pipe, so as to detect the amount of particulates contained in the exhaust gas; and
   the particulate detection apparatus is connected to the particulate sensor via a gas flow passage through which the gas supplied from the gas supply section flows.

10. A particulate detection system comprising a particulate detection apparatus and a particulate sensor connected thereto, the particulate sensor comprising first and second gas introduction through holes and a detection section, the particulate detection apparatus controlling the particulate sensor for detecting an amount of particulates contained in a gas under measurement and including a gas supply section for supplying a gas different from the gas under measurement via the first gas introduction through hole of the particulate sensor to a detection section of the particulate sensor into which the gas under measurement is introduced via the second gas introduction through hole different from the first gas introduction through hole, the particulate gas detection apparatus comprising:
   gas detection means for detecting at least one of flow rate and pressure of the gas supplied from the gas supply section to the particulate sensor; and
   maintenance means for maintaining, based on the result of the detection by the gas detection means, a consistent accuracy in detecting the amount of particulates by the particulate sensor.

* * * * *